United States Patent [19]
Radford et al.

[11] Patent Number: 5,587,527
[45] Date of Patent: Dec. 24, 1996

[54] HANDHELD DENSITY METER

[76] Inventors: Neal T. Radford, 2119A Lakepark Dr., Smyrna, Ga. 30080; Roy J. Waddle, 2262K Northwest Pkwy., Marietta, Ga. 30067

[21] Appl. No.: 468,230

[22] Filed: Jun. 6, 1995

Related U.S. Application Data

[63] Continuation of Ser. No. 59,104, May 10, 1993, abandoned.

[51] Int. Cl.$^6$ .................................................. G01N 9/28
[52] U.S. Cl. .................................................. 73/439
[58] Field of Search .................. 73/299, 300, 301, 73/302, 292, 438, 439; 374/148, 147, 142

[56] References Cited

U.S. PATENT DOCUMENTS

| | | | |
|---|---|---|---|
| 1,457,406 | 6/1923 | Stancliffe | 73/439 |
| 1,460,134 | 6/1923 | Johlin | 73/439 |
| 2,394,549 | 2/1946 | Howe | 73/439 |
| 2,577,548 | 12/1951 | Vetter | 73/439 |
| 2,668,438 | 2/1954 | Marquardt | 73/439 |
| 2,755,669 | 7/1956 | Beard | 73/439 |
| 2,878,675 | 3/1959 | Crabbe | 73/439 |
| 2,898,763 | 8/1959 | Jawett | 73/439 |
| 3,451,273 | 6/1969 | Ludlow | 73/440 |
| 3,453,891 | 7/1969 | Kapff | 73/439 |
| 3,460,394 | 8/1969 | Cryer | 73/439 |
| 3,754,445 | 8/1973 | Pavlo | 73/441 |
| 4,132,110 | 1/1979 | Muramoto | 73/32 A |
| 4,307,609 | 12/1981 | Rosenblum | 73/439 |
| 4,393,705 | 7/1983 | Eidschun | 73/439 |
| 4,630,478 | 12/1986 | Johnson | 73/438 |
| 4,815,093 | 3/1989 | Wollermann-Windgasse | 372/62 |
| 4,949,572 | 8/1990 | Wilen et al. | 73/53.01 |
| 5,115,679 | 5/1992 | Uhlarik | 73/438 |

*Primary Examiner*—Christine K. Oda
*Attorney, Agent, or Firm*—Louis T. Isaf, P.C.

[57] ABSTRACT

A method and handheld apparatus for the measurement of liquid density comprising a handheld enclosure which encases a differential pressure transducer having each pressure orifice connected by separate tees to separate hollow bubble tubes. Each bubble tube is connected on one end to a common micro-pump providing a balanced and relatively constant gas flow in each hollow bubble tube. The other ends of the bubble robes are terminated outside of the enclosure at relatively fixed and different distances from the enclosure in an arrangement that provides for the bubble tubes to be encased in a free hanging probe that will hang substantially vertical and will access liquid chamber diameters down to ¼ inch. The apparatus measures density by vertically orienting the open ends of each hollow bubble tube in a liquid and measuring the differential pressure at the open ends of the bubble tubes created by the weight of the liquid at their respective depths. The apparatus also compromises an electronic circuit which takes the output signal from the differential pressure transducer, manipulates it and displays a properly calibrated and steady reading.

14 Claims, 3 Drawing Sheets

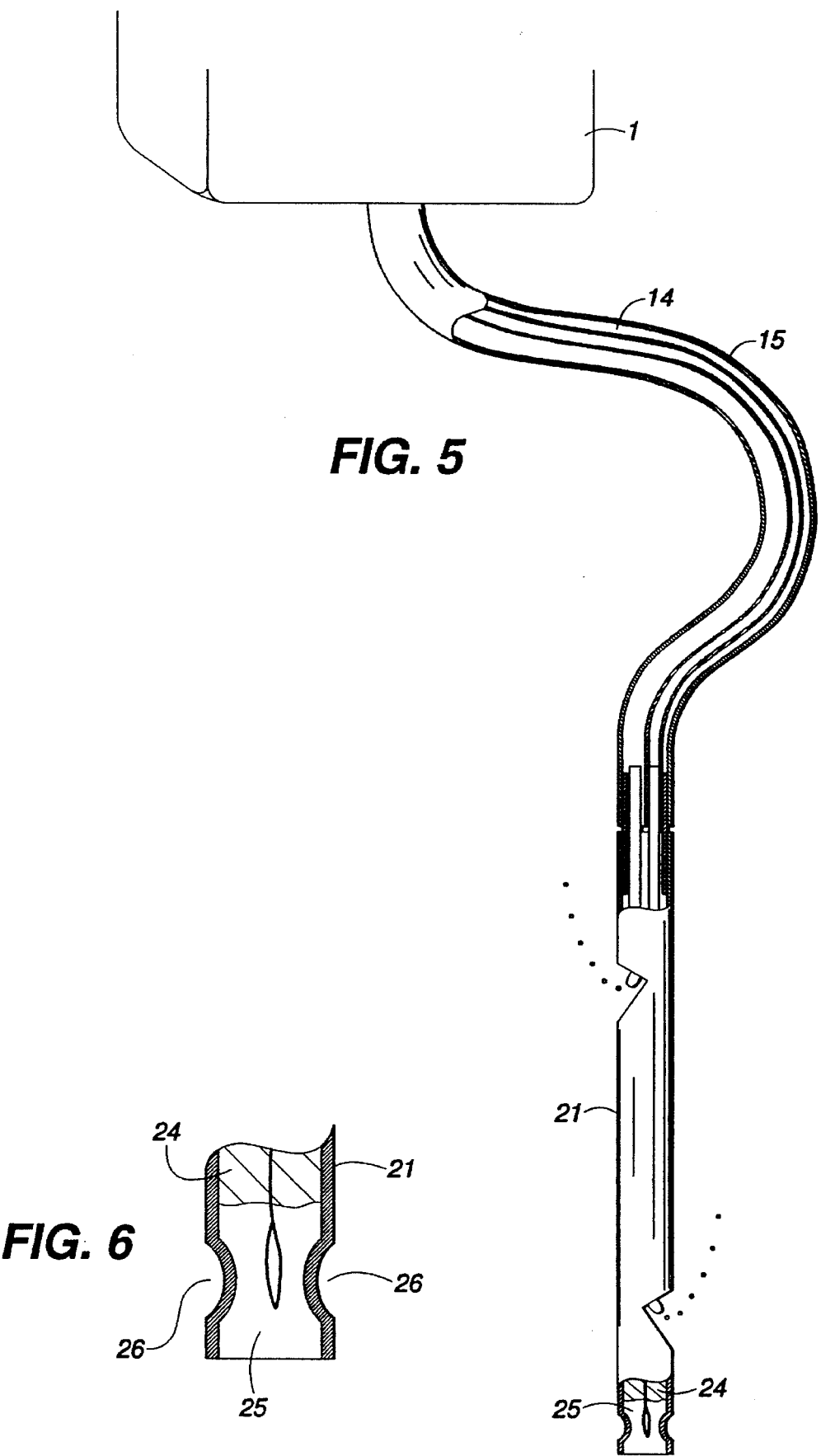

HANDHELD DENSITY METER

This application is a continuation of application Ser. No. 08/059,104, filed May 10, 1993, now abandoned.

BACKGROUND OF THE INVENTION

This invention relates to a method and handheld apparatus for the measurement of liquid density in a static or agitated column of liquid. This invention has particular application to the measurement of the density or specific gravity of sulfuric acid in a flooded lead-acid battery as is commonly used in the motive power, telecommunications, uninterruptible power supply, nuclear and automotive industries.

As can be seen by references in this field of invention, there are many uses for the measurement of liquid density. There are also many means by which liquid density can be measured. The specific field of this invention pertains to the measurement of liquid density by reading the differential pressure at two vertically disposed positions. It is an accepted principle that the differential pressure between two points vertically disposed in a column of liquid is the product of the vertical distance between them and the density of the liquid. If the distance is kept constant, the differential pressure will be a linear function of density.

While the use of this invention applies itself to many different applications, it is specifically useful in the measurement of sulfuric acid density in a flooded lead-acid battery. Regular maintenance on this type of battery requires the frequent measurement of voltage, temperature and liquid specific gravity. In many cases, as many as 240 individual batteries comprise a system in one location. An added complication to the requirements of the present invention includes the limited space between the top of one battery and the bottom of another in a battery rack. Another is the requirement to take the measurement in a draw tube located at the corner of most batteries, having a diameter as small as ¼ inch and extending up to ten inches vertically into the battery's liquid.

In review of prior art, only three different means of liquid density measurement have been incorporated into a handheld device. These three are: 1) The float style hydrometer; 2) Frequency measurement of a vibrating liquid sample; and 3) Optical refraction. The following references are cited as examples of these means of measurement: U.S. Pat. Nos. 3,451,273, 3,754,445 and 4,132,110.

The disadvantages of these devices are many. The float style hydrometer and the vibration methods require drawing samples into a separate chamber for the reading to take place. This is both time consuming and unsafe when dealing with hazardous chemicals like sulfuric acid. The optical refraction method has been adapted so as not to require the removal of a sample but is not designed such that it can enter the draw tube of a battery. The float style hydrometer has been adapted for use in this application but requires a reading from a tightly graduated scale which is prone to calibration inaccuracies as well as human reading error. The mechanical nature of this device makes it unadaptable to electronic manipulation such as data logging for saving or communicating information to a central processing unit. The vibration device is also prone to error due to its tendency to be fouled by gas bubbles in the tubes.

Other references cited give specific attention to a device known as a "gas bubbler". The original "gas bubbler", cited by references U.S. Pat. Nos. 1,457,406 and 1,460,134, do not provide for a handheld device nor would either of them be well applied to a handheld device because of their analog readings and inability to provide the degree of accuracy required by many applications. All other developments in the "gas bubbler" have not included the necessary elements to allow portability and accuracy in the same invention. References U.S. Pat. Nos. 2,394,549, 2,577,548 and 4,393,705 are further examples of these inadequacies.

Unlike other references cited, the present invention provides numerous advantages over previous methods. None of the references cited overcome the disadvantage of pulling a sample of liquid into a separate chamber except for one device which requires a much larger diameter for access to the chamber of the liquid being measured. Alternatively, a particular embodiment of the apparatus can access liquid chambers with openings down to ¼ inch in diameter. This is particularly required for accessing sulfuric acid in a battery or for being directly interchangeable with a typical float style hydrometer. Surpassing the typical float style hydrometer, the present invention can access and measure density in a column of liquid down to ¼ inch in diameter without drawing liquid and can do so in a physical environment where there is limited clearance with another battery or other object above.

Further, the ability to take almost instantaneous readings without extracting a liquid sample has two advantages. First, a significant time savings can be seen in a job requiring the reading of numerous liquid samples. Second, the handling of hazardous chemicals can be avoided. This is particularly important in the example of sulfuric acid in a flooded lead-acid battery.

Another particular embodiment of the present invention provides for a higher degree of accuracy in a handheld device. It is understood by those skilled in the art that the characteristics of how the gas bubbles form at the opening orifice of a bubble tube in a liquid can significantly affect the accuracy of the differential pressure being measured by the differential pressure transducer. As the orifices move closer together for compactness, the percentage effects of bubble formation to overall accuracy become greater. Further, the constant removal, drying and rewetting of the orifices are cause for more error as would be characteristic of a handheld device.

Agitation, viscosity and surface tension have all been cited in previous inventions as being reasons for inaccuracies as these all affect how consistently bubbles are formed and released at the opening. References U.S. Pat. Nos. 2,668,438 and 2,755,669 both address this problem by offering embodiments which are intended to dampen pressure fluctuations and achieve greater consistency in bubble formation. The embodiments described in these references do not address the requirement to produce accurate results in a bubble tube arrangement that is small enough to enter a ¼ inch diameter draw tube as would be found on a flooded lead-acid battery. Further, these references offer embodiments that are to sensitive to slight changes in angle of the bubble tube opening orifice as would be characteristic of a handheld device.

Another reference, U.S. Pat. No. 4,949,572, addresses the bubble formation problem by taking a reading only after stopping gas flow at a controlled point. This would not be practical in a handheld device due to the moveability of the probe. A preferred embodiment of this invention achieves the required accuracy with fewer components resulting in higher reliability and lower cost.

Further, most density measurement applications do not require a very high degree of accuracy. The present invention can sustain readings of liquid density with an accuracy and repeatability of up to plus or minus 0.002 grams per cc. This meets or exceeds the requirements of most density measurement applications.

SUMMARY OF THE INVENTION

In accordance with the present invention, the above-described and other disadvantages of the prior art are overcome by providing a density meter comprising an enclosure which can be handheld and a method for measuring the differential pressure created by two separate bubble tubes extending from said enclosure whose outlet orifices are positioned at different lengths from the enclosure. Each bubble tube is connected to a common and relatively constant gas supply and connected across the separate measurement orifices of a differential pressure transducer. The differential pressure transducer provides a output signal that; can be calibrated and displayed to read the density of a liquid in which the open ends of the bubble tubes are inserted.

The relatively constant gas supply for the bubble tubes comprises a micropump, a volume chamber, a tee and two restrictors of different size restriction. A micropump of the size that would fit into a handheld enclosure generally has a flowrate that fluctuates with pump cycles causing pressure waves. To overcome this, the micropump supplies gas to a relatively large diameter tube which serves as a volume chamber to dampen short interval fluctuations in the gas flow output. A tee is installed after the volume chamber to separate the gas flow to both bubble tubes. The restrictors are installed in the bubble tubes after the tee and before the differential pressure transducer increasing the back pressure on the volume chamber and allowing gas to collect. The restrictor having the greatest restriction is placed in the lower pressure bubble tube so as to balance the gas flow when the bubble tubes are immersed into a liquid. If the same restrictor values were used, gas would only flow from the lower pressure bubble tube while immersed in a liquid, taking the least resistant path.

Another embodiment of the present invention also provides for a handheld density meter which has bubble tube orifices which provide for greater accuracy in a handheld device or any application requiring the orifices to be relatively close together. The orifices comprise several characteristics which diminish the effects of agitation, viscosity, and surface tension while being easily and compactly manufactured. The orifice has:

1) A relatively round shape with an internal diameter large enough to minimize the effects of surface tension inside the orifice near the opening and small enough to provide adequate accuracy when the higher and lower pressure orifices could be relatively close together;

2) A substantially sharp edge at the opening to cause the liquid being measured to more consistently contact the orifice and not interfere with the exiting gas;

3) An angle of opening such that the edge is at a substantially right angle with the centerline of the gas flow and the centerline of gas flow is neither sustantially vertical nor horizontal (A moderate angle allows for more consistent bubble release even when the device may be at a slight angle in the fluid.); and 4) A relatively smooth internal diameter so as to minimize the surface area to which liquid can adhere. These characteristics are mutually exclusive and all provide for increased accuracy in a handheld density meter.

Another embodiment of the present invention also provides for a handheld density meter bubble tube arrangement comprising both rigid and flexible probe sections. The orifices and lower end of the bubble tubes are encased in a rigid section. The diameter of the rigid section can be fashioned so as not to exceed ¼ inch diameter making it accessible to the draw tube of a battery or other small openings. The rigid section of the probe provides for a more precise distance between the opening orifices of the bubble tubes.

The upper end of the rigid section is connected to a flexible section which comprises two separate flexible tubes having internal diameters of relatively the same size as those in the rigid section. The flexible tubes are of such a material that they will resist, kinking which would cause inaccuracies in the density reading. Conventional means is provided to connect the upper and lower ends of the flexible tubes.

The flexible tubes provide three distinct advantages: 1) The rigid and relatively heavier section of the probe will always hang substantially vertical in any liquid keeping the distance between the open ends of the bubble tubes relatively fixed regardless of the enclosure's position thus improving accuracy; 2) The rigid section of the probe can enter the draw tube on a stationary battery even when limited space is available above the entrance to the draw tube and still extend to its required depth for a reading which can be up to ten inches below the entrance (A long rigid probe could not do this.); and 3) The rigid section of the probe can be clipped to the side of the enclosure for carrying, minimizing the risk of damage that would exist with a full ten-inch rigid probe.

A preferred embodiment of the present invention also provides for the flexible upper section of the probe to be configured such that one bubble tube travels down the inside of another bubble tube. The centerline of one bubble tube is essentially concentric with the other. Means is provided at both the upper and lower ends to insure both gas flow paths are independent. By routing the bubble tubes in this way, the following advantages are gained: (1) The flexible upper section of the probe will bend more easily about its centerline than two separated flexible tubes allowing the rigid lower section to hang more vertical; and (2) The concentric arrangement provides for less overall restriction to the gas flow because it uses space more effectively. The cross-sectional areas of the gas flow paths can be made larger allowing the routing of wires for a thermocouple or other such device without interfering with the gas flow path.

Another embodiment of the present invention also provides a handheld density meter bubble tube arrangement that allows for temperature compensation of the density measurement in a probe with all the features as described above. A temperature measurement device (e.g. a thermocouple) is nested inside of the rigid probe section at the lowest point while still being protected by the outside casing of the rigid body. The lead wires are of such a diameter that they can be routed inside of the bubble tube with the outer most gas flow path. A method is provided in the assembly of the rigid section to allow the lead wires to exit from the inside of the bubble tube without interfering with the flow of gas from the outlet orifice of the bubble tube in which the lead wires are routed. A means is provided within the enclosure for the lead wires to exit from the inside of the bubble tube without interfering with the flow of gas. A means for reading the temperature on a display is provided as well as a means to electronically adjust the liquid density reading to compensate for variability of the liquid density with temperature.

It is an object of this invention to provide an improved method and apparatus for the handheld measurement of liquid density in a column of liquid by measuring the differential pressure between two vertically disposed points.

It is an object of this invention to provide an improved method and apparatus for the handheld measurement of liquid density in a column of liquid without removing a sample of liquid, where the access to said liquid chamber may be no larger than ¼ inch diameter and the space above the liquid chamber is limited.

It is an object of this invention to provide an improved method and apparatus for the handheld measurement of liquid density in a column of liquid that also provides for the measurement of the temperature of the liquid with means to compensate for the variability of the liquid density with temperature.

It is an object of this invention to provide an improved method and apparatus for the handheld measurement of liquid density in a column of liquid which is less expensive, sturdier, easier to maintain, simpler, more accurate, and quicker than existing methods and apparatus.

The above-described and other advantages of the present invention will be better understood from the following detailed description when considered in connection with the accompanying drawings.

BRIEF DESCRIPTION OF DRAWINGS

In the drawings which are to be regarded as merely illustrative:

FIG. 5 shows, with parts sectioned, the detailed construction of one preferred embodiment of the present invention wherein the upper section of the bubble tube arrangement comprises concentric flexible bubble tubes.

FIG. 6 is an exploded cross-sectional view of the rigid section serving to illustrate the method for installing the temperature measurement device.

DESCRIPTION OF THE INVENTION

Figure 2:
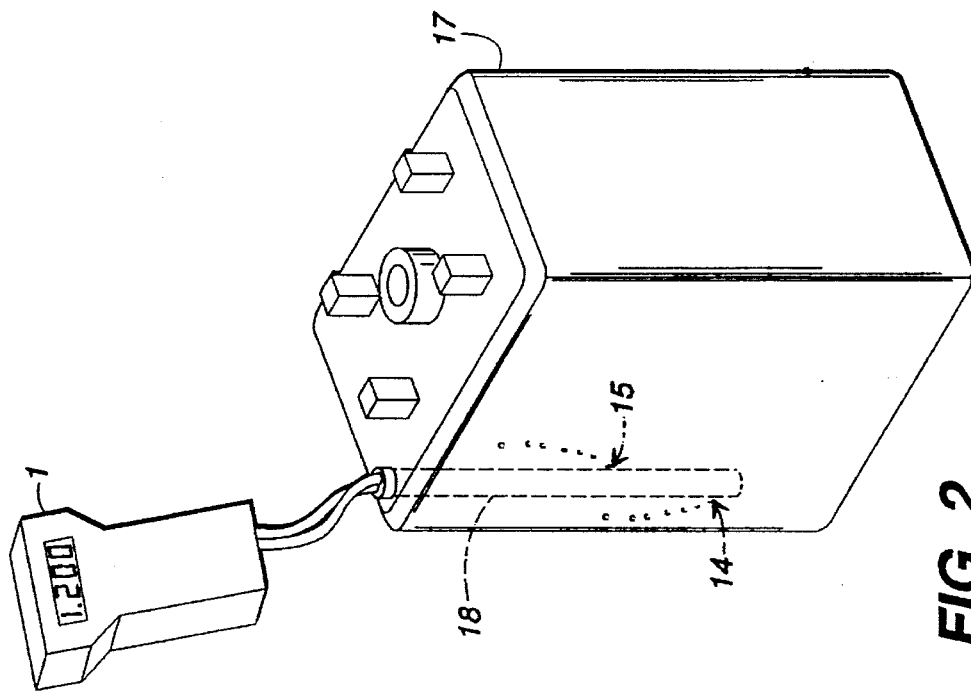
FIG. 2 is an illustration of a particular embodiment of the present invention in common use in a flooded lead-acid battery.

In the figures the same reference numerals are used to indicate the same or similar parts or components.

Figure 1:
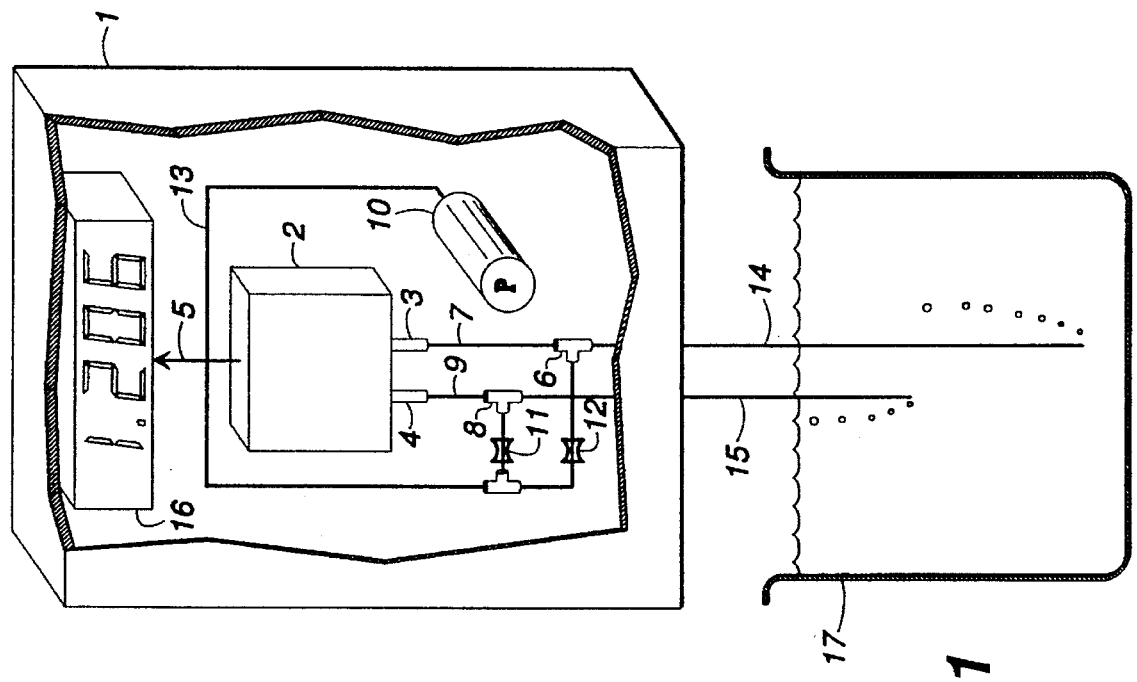
FIG. 1 is a schematic drawing of the handheld device illustrating a basic embodiment of the invention.

Referring to FIG. 1, The basic embodiment of the present invention is shown schematically. The apparatus shown in FIG. 1 gives a reading of relative density using a handheld device. Enclosure 1 is used to provide a structure for the fixed mounting of a differential pressure transducer 2. The differential pressure transducer 2 comprises a higher pressure orifice 3 and a lower pressure orifice 4 and provides an output signal 5 proportional to the difference in the two input pressures. The higher pressure orifice 3 is connected to the higher pressure hollow bubble tube 14 by way of a hollow measurement tube 7 and tee 6. Similarly, the lower pressure orifice 4 is connected to the lower pressure hollow bubble tube 15 by way of a hollow measurement tube 9 and tee 8. Each bubble tube 14, 15 is connected to a common gas pump 10 having a relatively constant gas flow by way of restrictors 11, 12 and volume chamber 13. The volume chamber 13 comprises a relatively larger diameter tubing long enough to provide sufficient volume to dampen short interval pressure fluctuations in the gas supply. It will be understood that the use of a volume chamber only enhances the accuracy of the present invention and is not necessary for its operation. The restrictors 11, 12 are sufficiently small enough to provide enough back pressure to pressurize the volume chamber 13. Means is provided to connect these components such that there is no gas leakage except that which is exiting the bubble tubes outside of the handheld enclosure. Restrictor 11 has a substantially higher restriction than restrictor 12 so that, when the outlet orifices are immersed into a fluid, gas will exit both orifices. If the restrictors were not balanced in this way, gas would take the least resistant path and only exit from the lower pressure orifice.

Each bubble tube 14, 15 extends outside the enclosure 1 to relatively fixed points such that the outlet orifice of the higher pressure hollow bubble tube 14 can be vertically oriented at a fixed point below the outlet orifice of the lower pressure hollow bubble tube 15 and immersed into a liquid 17 in order to take a reading. The output signal 5 is connected electrically to an electronic circuit 16 that provides a means to offset, scale, average and display the output signal of the differential pressure transducer to provide a steady and properly scaled output for reading the measurement of liquid density.

Referring to FIG. 2, an embodiment of the present invention is illustrated in a typical application in the measurement of liquid density. The apparatus is shown taking a reading of density in the electrolyte of a flooded lead-acid battery 17. The battery 17 comprises a draw tube 18 situated in its upper corner. It will be understood that the diameter of the draw tube 18 is usually not more than 5/16 inch which is a limiting factor for a particular embodiment of the present invention. The higher pressure hollow bubble tube 14 and the lower pressure hollow bubble tube 15 extend through the draw tube 18 in order to take a reading. It will also be understood that the draw tube extends below the level of the liquid being measured.

Figure 4:
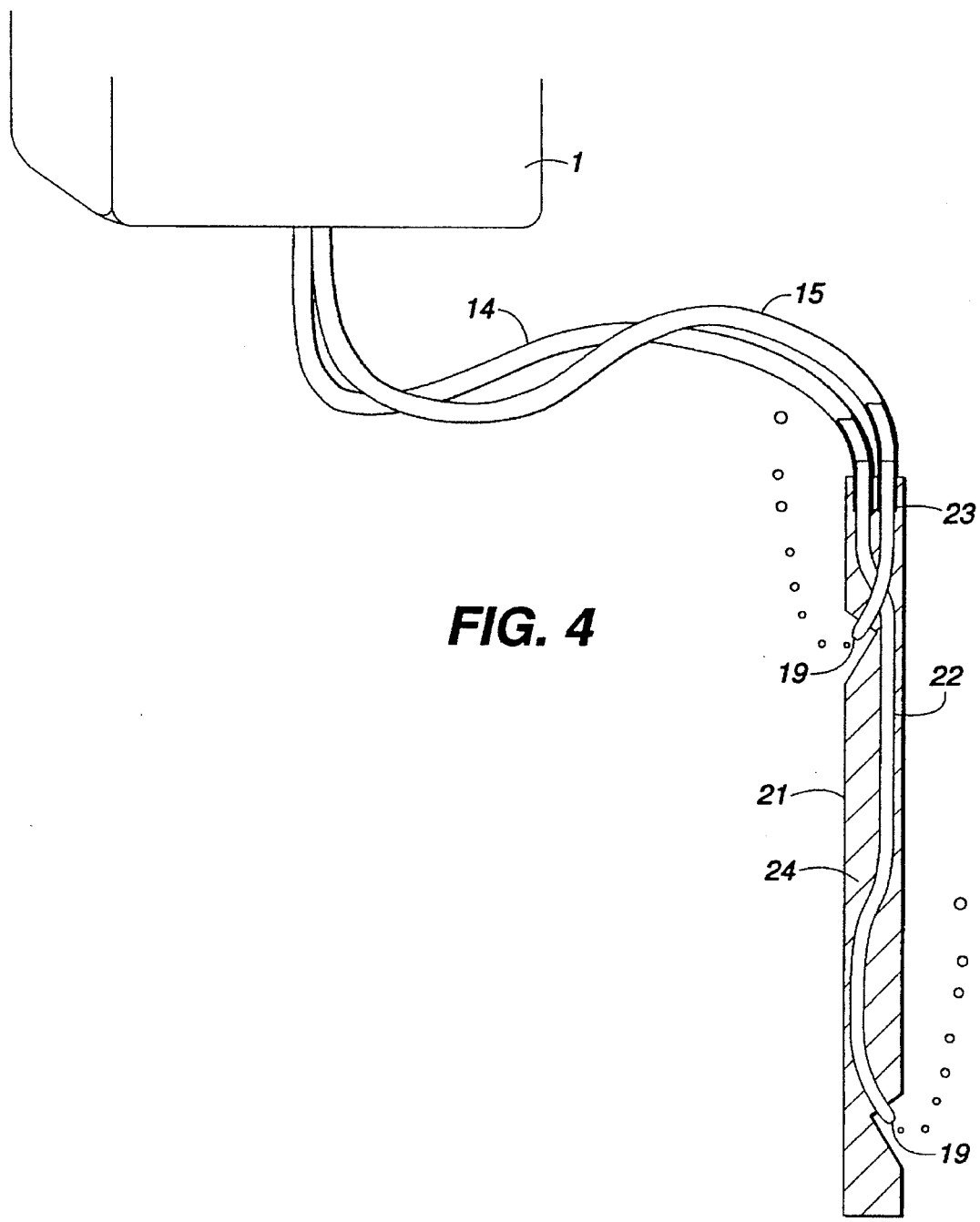
FIG. 4 shows, with parts sectioned, the detailed construction of one particular embodiment according to the present invention wherein the upper section of the bubble tube arrangement is flexible and other features are provided to create accessibility to the draw tube on flooded lead-acid batteries.
Figure 3:
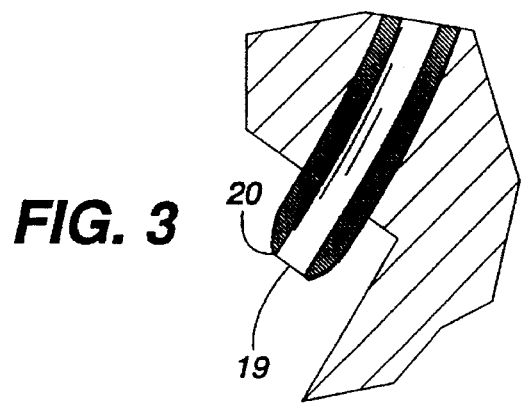
FIG. 3 shows, with parts sectioned, the detailed construction of a particular embodiment wherein the bubble tube orifices are configured for improved accuracy.

Referring to FIG. 3, this illustration shows a preferred embodiment of the invention wherein, the bubble tube outlet orifices 19 are configured for improved accuracy. It will be understood that both the higher and lower pressure bubble tube outlet orifices 19 as shown in FIG. 4 are to be configured in the manner depicted and described. The outlet orifice 19 comprises hollow tubing of a relatively small internal cross-sectional area. To improve the accuracy of the outlet orifices 19, the end of the tubing is formed having a substantially uniform and sharp edge 20. The sharp edge eliminates the opportunity for fluid contacting the face of the orifice and interfering with the formation of bubbles. It is understood by those skilled in the art that, with all other factors constant, accuracy is proportional to the consistency in which bubbles are released. Further, the sharp edge can be formed by tapering the inside edge outward unlike that shown by FIG. 3.

It will be understood that the wall thickness is not important with respect to improving accuracy. A wall thickness should be selected which is large enough so that the tubing can be bent easily but small enough to minimize the fabricating effort required. An extremely thin wall thickness without mechanically tapering could provide enough sharpness and therefore enough accuracy to be feasible. Tapering the tubing provides for a greater wall thickness along the other portions of the tubing which may be advantageous for bending.

A second characteristic that improves accuracy is that the angle of the edge 20 be positioned at a substantially right angle to the longitudinal centerline of the hollow tubing and that the centerline of the gas flow be neither substantially vertical nor substantially horizontal. Again, this has been shown empirically to improve the consistency of bubble formation over other configurations. An approximate 30 degree angle of the centerline of the gas flow from vertical has been found to provide the most consistent results.

Further, the internal cross-section dimension of the tubing should be of a size large enough to prevent interference and blockage by a fluid's surface tension. However, the larger the internal dimension, the greater the error associated with the fluctuations in bubble size. An internal diameter of approximately 0.050 inches on a relatively round tube has provided the best empirical results. The use of round hollow tubing is preferred due to the ease in which it can be fabricated.

A final characteristic which improves the accuracy of the present invention is that the internal surface of the orifices 19 be relatively smooth. It is understood by those skilled in the art that, while immersed, fluid will enter the inside of the outlet orifices even with gas flowing outward. A relatively rough surface will allow fluid to adhere to the walls and interfere with the flow of gas and the bubble formation process. It will also be noted that the outlet orifice should be clear of any obstruction that may interfere with bubble release.

Referring to FIG. 4, this drawing shows a particular embodiment of the invention wherein, the bubble tubes 14, 15 shown in FIG. 1 are replaced with a bubble tube arrangement comprising a relatively flexible upper section and a relatively rigid lower section 21. Extending from enclosure 1 is a higher pressure bubble tube 14 and a lower pressure bubble tube 15. Each tube being relatively flexible and having an internal diameter sufficiently large enough to not be blocked by liquid entering the bubble tubes as would be the case if the apparatus mistakenly was not pumping gas while in the liquid. Being large enough allows the bubble tubes to be flushed of all contaminating liquid once the flow of the gas was re-established. The flexible bubble tubes must also be of a material that resists kinking when bent on a relatively tight radius. The length of the flexible bubble tubes is only important given the particular requirements of the container in which the density measurement is being taken. The outside diameter of the flexible bubble tubes must be small enough to maintain adequate flexibility to allow the rigid lower section 21 to hang substantially vertical and small enough to access the liquid container's opening.

Conventional means is provided to connect flexible bubble tubes 14, 15 to the higher pressure rigid bubble tube 22 and the lower pressure rigid bubble tube 23. Each rigid bubble tube extends into the rigid section with the outlet orifice of the lower pressure rigid bubble tube 23 terminating at a point substantially fixed and vertical above the outlet orifice of the higher pressure rigid bubble tube 22. The rigid bubble tubes are encased in a potting compound 24 which serves to hold the tubes in place as well as add weight to the rigid section to ensure the most vertical position possible while immersed in the liquid to be measured. The outlet orifices of the rigid bubble tubes 22, 23 are positioned substantially away from the outside edge of the rigid section so as not to let an object near the outlet orifices interfere with the release of bubbles.

Referring to FIG. 5, this drawing shows a preferred embodiment of the bubble tube arrangement shown in FIG. 4 wherein the bubble tubes 14, 15 in the upper flexible section are routed concentrically with respect to each other. In this figure, the higher pressure bubble tube 14 is routed within the lower pressure bubble tube 15. Means is provided to seal and isolate the gas flow paths from each other and the environment. Similar means is provided at the upper end inside the enclosure 1 and the lower end where the flexible section connects to the rigid lower section 21. In the gas flow path for lower pressure bubble tube 15, enough space exists to route the lead wires for thermocouple 25 without causing excess restriction. This embodiment is described in FIG. 6.

Referring to FIG. 6, this drawing shows a particular embodiment of the invention, wherein, a temperature measurement device 25 is embedded into the potting compound 24 and exposed to the fluid at the lower most end of the rigid section 21. The body of the rigid section is used to protect the device 25 and vent holes 26 allow fluid to come in contact with the device. Means is provided to allow the lead wires of the temperature measurement device 25 to exit the flow path of the bubble tube without interfering with the pressure or relatively constant flow of gas within the bubble tube. Finally, a surface treatment can be provided to chemically protect the sensing point of the temperature measurement device 25 from the liquid as required.

We claim:

1. In a density meter comprising a gas pump; a tube assembly including an elongated first bubble tube defining a first tube interior into which the gas pump discharges and an elongated second bubble tube defining a second tube interior into which the gas pump also discharges, wherein the first bubble tube includes a first outlet and the second bubble tube includes a second outlet, and wherein the first outlet is located at a first elevation and the second outlet is located at a second elevation that is different from the first elevation when the first bubble tube is oriented vertically with the second bubble tube; a pressure measuring assembly cooperating with the first tube interior and the second tube interior for measuring a differential pressure defined between the first tube interior and the second tube interior; and a readout device for visually displaying data that corresponds to the differential pressure; wherein the improvement comprises:

the density meter further comprising an enclosure structure constructed and arranged to be handheld, wherein said enclosure structure houses the gas pump, the pressure measuring assembly, and the readout device, the tube assembly extending from said enclosure structure and being constructed and arranged so that an elongated section of the second bubble tube is disposed within an elongated section of the first tube interior.

2. The density meter of claim 1, wherein the first bubble tube includes an elongated, substantially flexible first upper section and an elongated, substantially rigid first lower section, wherein the second bubble tube includes an elongated, substantially flexible second upper section and an elongated, substantially rigid second lower section, wherein said first lower section and said second lower section are joined over a substantial length, and wherein the tube assembly is constructed and arranged so that when said first lower section and said second lower section are allowed to hang freely from said first upper section and said second upper section, said first lower section and said second lower section hang substantially vertically.

3. The density meter of claim 1, wherein the first bubble tube and the second bubble tube are connected such that a distance is defined between the first outlet and the second outlet such that said distance is substantially fixed and constant.

4. The density meter of claim 1, further comprising a temperature measurement device including
   a sensor displaced from the first outlet of the first bubble tube, and
   lead wires extending between said sensor and said enclosure structure, wherein said lead wires extend through an elongated section of the first tube interior.

5. The density meter of claim 4,
   wherein the tube assembly further includes an elongated, substantially rigid member including a top end and a bottom end,
   wherein the first bubble tube is at least partially encased in said rigid member,
   wherein the second bubble tube is at least partially encased in said rigid member, and
   wherein said sensor is connected to said rigid member proximate to said bottom end of said rigid member.

6. The density meter of claim 1,
   wherein the tube assembly further includes an elongated, substantially rigid free hanging member including an exterior that includes a top end and a bottom end,
   wherein the first bubble tube includes
      an elongated, substantially flexible first upper tube that extends from said enclosure structure and includes a first terminus distant from said enclosure structure, and
      a downstream, elongated, first lower tube,
         wherein said first lower tube is at least partially encased in said rigid free hanging member, and
         wherein said first lower tube includes
            an inlet end extending from said top end of said rigid free hanging member and in fluid communication with said first terminus of said first upper tube, and
            an outlet end accessible at, and proximate to, said exterior of said rigid free hanging member distant from said top end of said rigid free hanging member, and
   wherein the second bubble tube includes
      an elongated, substantially flexible second upper tube that extends from said enclosure structure and includes a second terminus distant from said enclosure structure, and
      a downstream, elongated, second lower tube,
         wherein said second lower tube is at least partially encased in said rigid free hanging member, and
         wherein said second lower tube includes
            an inlet end extending from said top end of said rigid free hanging member and in fluid communication with said second terminus of said second upper tube, and
            an outlet end accessible at, and proximate to, said exterior of said rigid free hanging member distant from said top end of said rigid free hanging member.

7. The density meter of claim 6, wherein said rigid member defines a substantial mass, whereby when said first lower section and said second lower section are allowed to hang freely from said first upper section and said second upper section, said first lower section and said second lower section hang substantially vertically.

8. The density meter as claimed in claim 1, wherein said second bubble tube and said first tube interior of said tube assembly have different diameters.

9. The density meter as claimed in claim 1, wherein said second bubble tube is the higher pressure bubble tube and said first bubble tube is the lower pressure bubble tube.

10. In a density meter comprising a gas pump; a tube assembly including an elongated first bubble tube defining a first tube interior into which the gas pump discharges and an elongated second bubble tube defining a second tube interior into which the gas pump also discharges, wherein the first bubble tube includes a first outlet and the second bubble tube includes a second outlet, and wherein the first outlet is located at a first elevation and the second outlet is located at a second elevation that is different from the first elevation when the first bubble tube is oriented vertically with the second bubble tube; a pressure measuring assembly cooperating with the and the second tube interior for measuring a differential pressure defined between the first tube interior and the second tube interior; and a readout device for visually displaying data that corresponds to the differential pressure; wherein the improvement comprises:
   the density meter further comprising an enclosure structure constructed and arranged to be handheld, wherein said enclosure structure houses the gas pump, the pressure measuring assembly, and the readout device,
   the tube assembly extending from said enclosure structure and being constructed and arranged so that an elongation of the second bubble tube is disposed within an elongated section of the first tube interior,
   wherein the tube assembly further includes an elongated, substantially rigid member including an exterior that includes a top end and a bottom end,
   wherein the first bubble tube includes
      an elongated, substantially flexible first upper tube that extends from said enclosure structure and includes a first terminus distant from said enclosure structure, and
      a downstream, elongated, first lower tube,
         wherein said first lower tube is at least partially encased in said rigid member, and
         wherein said first lower tube includes
            an inlet end extending from said top end of said rigid member and in fluid communication with said first terminus of said first upper tube, and
            an outlet end accessible at said exterior of said rigid member distant from said top end of said rigid member, and
   wherein the second bubble tube includes
      an elongated, substantially flexible second upper tube that extends from said enclosure structure and includes a second terminus distant from said enclosure structure, and
      a downstream, elongated, second lower tube,
         wherein said second lower tube is at least partially encased in said rigid member, and
         wherein said second lower tube includes
            an inlet end extending from said top end of said rigid member and in fluid communication with said second terminus of said second upper tube, and
            an outlet end accessible at said exterior of said rigid member distant from said top end of said rigid member,
      wherein said second terminus of said second upper tube is disposed within said first upper tube, wherein said second terminus of said second upper tube is connected to said inlet end of said second lower tube, and wherein said first terminus of said first upper tube is connected to and encircles said top end of said rigid member such that said first upper tube is in fluid communication with said inlet end of said first lower tube.

11. The density meter of claim 6, wherein said outlet end of said first lower tube and said outlet end of said second lower tube extend from, and are proximate to, said exterior of said rigid free hanging member, and are distant from said top of said rigid free hanging member.

12. The density meter of claim 11, wherein said rigid member defines an elongated axis, wherein said outlet end of said first lower tube defines an elongated axis that defines an angle with respect to said elongated axis of said rigid member, and wherein said outlet end of said second lower tube defines an elongated axis that defines an angle with respect to said elongated axis of said rigid member.

13. In a density meter comprising a gas pump; a tube assembly including an elongated first bubble tube defining a first tube interior into which the gas pump discharges and an elongated second bubble tube defining a second tube interior into which the gas pump also discharges, wherein the first bubble tube includes a first outlet and the second bubble tube includes a second outlet, and wherein the first outlet is located at a first elevation and the second outlet is located at a second elevation that is different from the first elevation when the first bubble tube is oriented vertically with the second bubble tube; a pressure measuring assembly cooperating with the first tube interior and the second tube interior for measuring a differential pressure defined between the first tube interior and the second tube interior; and a readout device for visually displaying data that corresponds to the differential pressure; wherein the improvement comprises:

the density meter further comprising an enclosure structure constructed and arranged to be handheld, wherein said enclosure structure houses the gas pump, the pressure measuring assembly, and the readout device, wherein the first bubble tube includes an elongated, tubular, substantially flexible first upper section extending from said enclosure structure, and an elongated, tubular, substantially rigid first lower section in fluid communication with said first upper section, wherein said first lower section includes the first outlet, and wherein the first outlet is distant from said first upper section, wherein the second bubble tube includes an elongated, tubular, substantially flexible second upper section, and an elongated, tubular, substantially rigid second lower section, wherein said second lower section includes the second outlet, and wherein the second outlet is distant from said second upper section, wherein an elongated section of said second upper section is disposed within an elongated section of said first upper section, wherein said first lower section and said second lower section are joined, wherein the tube assembly further includes an elongated, substantially ridig member including an exterior that includes a top end an a bottom end, wherein said first upper section includes a first terminus distant from said enclosure structure, wherein said first lower section is at least partically encased in said rigid member, wherein said first lower section includes an inlet end extending from said top end of said rigid member and in fluid communication with said first terminus of said first upper section, and an outlet end accessible at said exterior of said exterior of said rigid member distant from said top end of said rigid member, and wherein said second upper section includes a second terminus distant from said enclosure structure, and wherein said second lower section is at least partially encased in said rigid member, and wherein said second lower section includes an inlet end extending from said top of said rigid member and in fluid communication with side second terminus of said second upper section, and an outlet end accessible at said exterior of said rigid member distant from said top end of said rigid member, and wherein the tube assembly is constructed and arranged so that when said first lower section and said second lower section are allowed to hang freely from said first upper section and said second upper section, said first lower section and said second lower section hang substantially vertically.

14. In a density meter comprising a gas pump; a tube assembly including an elongated first bubble tube defining a first tube interior into which the gas pump discharges and an elongated second bubble tube defining a second tube interior into which the gas pump also discharges, wherein the first bubble tube includes a first outlet and the second bubble tube includes a second outlet, and wherein the first outlet is located at a first elevation and the second outlet is located at a second elevation that is different from the first elevation when the first bubble tube is oriented vertically with the second bubble tube; a pressure measuring assembly cooperating with the first tube interior and the second tube interior for measuring a differential pressure defined between the first tube interior and the second tube interior; and a readout device for visually displaying data that corresponds to the differential pressure; wherein the improvement comprises:

the density meter further comprising an enclosure structure constructed and arranged to be handheld, wherein said enclosure structure houses the gas pump, the pressure measuring assembly, and the readout device, wherein the first bubble tube includes an elongated, tubular, substantially flexible first upper section extending from said enclosure structure, and an elongated, tubular, substantially rigid first lower section in fluid communication with said first upper section, wherein said first lower section includes the first outlet, and wherein the first outlet is distant from said first upper section, wherein the second bubble tube includes an elongated, tubular, substantially flexible second upper section, and an elongated, tubular, substantially rigid second lower section, wherein said second lower section includes the second outlet, and wherein the second outlet is distant from said second upper section, wherein said first lower section and said second lower section are joined, wherein the tube assembly is constructed and arranged so that when said first lower section and said second lower section are allowed to hang freely from said first upper section and said second upper section, said first lower section and said second lower section hang substantially vertically, wherein the tube assembly further includes an elongated, substantially rigid member including an exterior that includes a top end and a bottom end, wherein said first upper section includes a first terminus distant from said enclosure structure, wherein said first lower section is at least partially encased in said rigid member, wherein said first lower section includes
- an inlet end extending from said top end of said rigid member and in fluid communication with said first terminus of said first upper section, and
- an outlet end accessible at said exterior of said rigid member distant from said top end of said rigid member, and wherein said second upper section includes a second terminus distant from said enclosure structure, and wherein said second lower section is at least partially encased in said rigid member, wherein said second lower section includes
- an inlet end extending from said top end of said rigid member and in fluid communication with said second terminus of said second upper section, and
- an outlet end accessible at said exterior of said rigid member distant from said top end of said rigid member, wherein an elongated section of said second upper section is disposed within an elongated section of said first upper section, wherein said second terminus of said second upper section is disposed within said first upper section, wherein said second terminus of said second upper section is connected to said inlet end of said second lower section, and wherein said first terminus of said first upper section is connected to and encircles said top end of said rigid member such that said first upper section is in fluid communication with said inlet end of said first lower section.

* * * * *